(12) United States Patent
Nelson et al.

(10) Patent No.: US 9,962,357 B2
(45) Date of Patent: May 8, 2018

(54) HALOGENATED ESTERS OF CYCLOPROPANATED UNSATURATED FATTY ACIDS FOR USE IN THE TREATMENT OF NEURODEGENERATIVE DISEASES

(71) Applicant: Blanchette Rockefeller Neurosciences Institute, Morgantown, WV (US)

(72) Inventors: Thomas J. Nelson, Morgantown, WV (US); Daniel L. Alkon, Chevy Chase, MD (US)

(73) Assignee: West Virginia University, Morgantown, WV (US)

( * ) Notice: Subject to any disclaimer, the term of this patent is extended or adjusted under 35 U.S.C. 154(b) by 0 days. days.

(21) Appl. No.: 15/028,487

(22) PCT Filed: Oct. 20, 2014

(86) PCT No.: PCT/US2014/061368
§ 371 (c)(1),
(2) Date: Apr. 11, 2016

(87) PCT Pub. No.: WO2015/058191
PCT Pub. Date: Apr. 23, 2015

(65) Prior Publication Data
US 2016/0256427 A1    Sep. 8, 2016

Related U.S. Application Data

(60) Provisional application No. 61/892,727, filed on Oct. 18, 2013, provisional application No. 61/896,735, filed on Oct. 29, 2013, provisional application No. 61/925,441, filed on Jan. 9, 2014, provisional application No. 61/925,449, filed on Jan. 9, 2014.

(51) Int. Cl.
*A01N 43/20* (2006.01)
*A01N 43/24* (2006.01)
*A61K 31/335* (2006.01)
*A61K 31/23* (2006.01)
*C07C 69/635* (2006.01)
*A61K 31/202* (2006.01)
*A61K 31/336* (2006.01)

(52) U.S. Cl.
CPC ............ *A61K 31/23* (2013.01); *A61K 31/202* (2013.01); *A61K 31/336* (2013.01); *C07C 69/635* (2013.01); *C07C 2602/02* (2017.05)

(58) Field of Classification Search
None
See application file for complete search history.

(56) References Cited

FOREIGN PATENT DOCUMENTS

| CN | 101 223 884 A | 7/2008 |
|---|---|---|
| CN | 101 608 402 A | 12/2009 |
| WO | WO 2010/014585 A1 | 2/2010 |
| WO | WO 2011/053870 A1 | 5/2011 |
| WO | WO 2013/071281 A1 | 5/2013 |

OTHER PUBLICATIONS

Bisogno et al., "Arachidonoylserotnin and Other Novel Inhibitors of Fatty Acid Amide Hydrolase," Biochemical and Biophysical Research Communications 248, 515-522 (1998).*
PCT International Search Report & Written Opinion, PCT/US2014/061368; dated Jan. 21, 2015.
Rezanka, T. et al.: "Novel brominated lipidic compounds from lichens of Central Asia", Phytochemistry, Pergamon Press, GB, vol. 51, No. 8, Aug. 1, 1999, 963-968.

* cited by examiner

*Primary Examiner* — Jared D Barsky
(74) *Attorney, Agent, or Firm* — Finnegan, Henderson, Farabow, Garrett & Dunner, LLP

(57) ABSTRACT

The present disclosure describes novel PKC-ε activators chosen from halogenated esters of unsaturated fatty acids derivatives thereof, including halogenated esters of both polyunsaturated and monunsaturated fatty acids and derivatives thereof. The disclosure further relates to compositions, kits, and methods for treatment using the halogenated esters.

26 Claims, 2 Drawing Sheets

HALOGENATED ESTERS OF CYCLOPROPANATED UNSATURATED FATTY ACIDS FOR USE IN THE TREATMENT OF NEURODEGENERATIVE DISEASES

This application claims priority to U.S. Provisional Patent Application Nos. 61/892,727, filed Oct. 18, 2013, 61/896,735, filed Oct. 29, 2013, 61/925,441, filed Jan. 9, 2014, and 61/925,449, filed Jan. 9, 2014, the contents of which are incorporated herein by reference.

PKC is one of the largest families of protein kinase enzymes and is composed of a variety of isoforms. Conventional isoforms include α, βI, βII, γ; novel isoforms include δ, ε, η, θ; and atypical isoforms include ξ, and ι/λ.

PKC enzymes are primarily cytosolic but translocate to the membrane when activated. In the cytoplasm, PKC is phosphorylated by other kinases or autophosphorylates. In order to be activated, some PKC isoforms (e.g., PKC-ε) require a molecule to bind to the diacylglycerol ("DAG") binding site or the phosphatidylserine ("PS") binding site. Others are able to be activated without any secondary binding messengers at all.

PKC activators that bind to the DAG site include, but are not limited to, bryostatin, picologues, phorbol esters, aplysiatoxin, and gnidimacrin. PKC activators that bind to the PS site include, but are not limited to, unsaturated fatty acids and their derivatives.

Once activated and translocated, PKC is anchored into the membrane by the anchoring protein RACK1. See, e.g., Mochly-Rosen et al. (1991) *Proc Natl Acad Sci USA* 88, 3997-4000; Nishizuka, Y. (1995) *FASEB J* 9, 484-496; Sklan et al. (2006) *Prog Neurobiol* 78, 117-134. RACK1 localizes PKC to its corresponding substrates for phosphorylation, thus making PKC functionally active and physiologically relevant.

Activated PKC participates in a variety of biological pathways. For example, PKC activates ELAV mRNA-stabilizing proteins and c-CAMP-response-element-binding ("CREB") proteins. PKC isoforms also play a regulatory role in amyloid precursor protein ("APP") processing and amyloid accumulation. For example, PKC-α and PKC-ε regulate APP processing by the non-amyloidogenic pathway, suggesting that decreases in these enzymes may lead to increases in A-beta synthesis and accumulation. Thus, PKC activators may be able to reduce levels of soluble A-beta and increase levels of soluble APP-α. PKC activators may also be able to reduce or eliminate amyloid plaques and neurofibrillary tangles.

PKC activators have been associated with prevention and treatment of various diseases and conditions. For example, PKC activators may allow for prevention and treatment of neurodegenerative diseases and conditions, neuroaffective diseases and disorders, cognitive impairments, and diseases and conditions associated with neuronal or synaptic loss. Indeed, PKC activators have been found to induce synapse formation. Moreover, PKC activators have been associated with improvement in, for example, memory and learning, including long-term memory.

In one specific example, PKC activators have demonstrated neuroprotective activity in animal models of Alzheimer's Disease ("AD"). See Etcheberrigaray et al., *Proc. Nat. Acad. Sci. USA*, 1992, 89: 7184-7188. AD is a neurodegenerative disorder that is characterized clinically by progressive decline of memory, cognition, reasoning, judgment, and emotional stability that gradually leads to profound mental deterioration and ultimately, death.

Pathologically, AD is associated with the accumulation of aggregated β-amyloid ("Aβ"), a 4 kDa peptide produced by the proteolytic cleavage of amyloid precursor protein ("APP") by β- and γ-secretases. As disclosed herein, oligomers of Aβ are considered to be most toxic while fibrillar Aβ is largely inert. Interestingly, monomeric Aβ is found in normal patients and has an as-yet undetermined function.

PKC activators can reduce the levels of Aβ and prolong survival of AD transgenic mice. See Etcheberrigaray et al., 1992, *Proc. Nat. Acad. Sci. USA*, 89: 7184-7188. PKC-ε was shown to be most effective at suppressing Aβ production. See Zhu et al., *Biochem. Biophys. Res. Commun.*, 2001, 285: 997-1006. Accordingly, isoform-specific PKC activators are highly desirable as potential anti-AD drugs and other conditions associated with Aβ production.

The earliest consistent cytopathological change in AD is loss of synapses. See Scheff et al., *Neurobiol. Aging*, 2006, 27: 1372-1384; and Marcello et al., *Eur. J. Pharmacol.* 2008, 585: 109-118. In fact, synaptic loss appears to be the only pathological finding in the brain that is closely correlated with the degree of dementia in AD patients. See Terry et al., *Ann. Neurol.*, 1991, 30: 572-580. To that end, evidence suggests that Aβ is involved in synaptic loss.

PKC activators may also be used to treat and prevent other diseases and conditions associated with synaptic loss and/or Aβ. For example, changes in dendritic spine density form the basis of learning- and memory-induced changes in synaptic structure that increase synaptic strength. Long-term memory, for example, is mediated, in part, by the growth of new dendritic spines to reinforce a particular neural pathway. By strengthening the connection between two neurons, the ability of the presynaptic cell to activate the postsynaptic cell is enhanced. Several other mechanisms are also involved in learning- and memory-induced changes in synaptic structure, including changes in the amount of neurotransmitter released into a synapse and changes in how effectively cells respond to those neurotransmitters (Gaiarsa et al., 2002). Because memory is produced by interconnected networks of synapses in the brain, such changes provide the neurochemical foundations of learning and memory.

Abnormalities in the number and morphology of dendritic spines have been observed in cognitive disorders, including attention deficit hyperactivity disorder, autism, mental retardation, and fragile X syndrome. For example, the brains of schizophrenic patients and people suffering from cognitive-mood disorders show a reduced number of dendritic spines in the brain areas associated with these diseases. In mental retardation and autism, the shape of the dendritic spines are longer and appear more immature. Similarly, the only microscopic brain anomaly found in fragile X syndrome, the most common inherited form of mental retardation and autism, is the presence of thin, elongated immature dendritic spines.

Fragile X Syndrome results from a mutation in the FMR1 gene found on the X chromosome, resulting in failure of the gene to express a protein required for normal neural development (fragile X mental retardation protein; FMRP). FMRP is a selective RNA-binding protein implicated in regulating transmission of mRNAs to dendrites. Delayed dendritic spine maturation was found in fragile X mental retardation patients as well as in Fmr1 knockout mice, indicating the functional requirement of FMRP in synaptic development. Lu et al., *Proc. Natl. Acad. Sci. U.S.A.*, 2008, 101(42):15201-06; and Comery et al., *Proc. Natl. Acad. Sci. U.S.A.*, 1997, 94 (10):5401-4. Autopsy results on several Fragile X patients have indicated that immature dendritic spine density (number per unit dendrite length) was higher in patient samples, suggesting a greater number of excitatory inputs to these neurons. Greenough et al., *Proc. Natl. Acad. Sci. U.S.A.* 2001, 98(13):7101-7106. This suggests that dendritic spine formation in Fragile X Syndrome fails to follow the normal maturational pattern of eliminating under-used synapses and altering the retained synapses to a more mature-appearing form of shorter, fuller spines.

FMRP also has been linked to Alzheimer's Disease. Beta-amyloid, the predominant protein found in the senile plaques of Alzheimer's disease and Down syndrome, is elevated in Fragile X mice and patients. Recent studies indicate that FMRP associates with the same mRNA coding region element as the amyloid precursor protein (APP), i.e., the protein that is cleaved into beta-amyloid plaques, and silencing FMRP promotes APP protein expression. Lee et al., *Nat Struct Mol Biol.*, 2010, 17(6):732-9. In addition, two micro-RNAs (short non-coding RNAs that suppress translation of specific mRNAs) that strongly affect synaptic structure and function have been shown to interact with FMRP. Edbauer et al., *Neuron,* 2010, 65(3):373-84.

As another example, persons who have suffered a brain injury show increased synthesis and expression of APP and its proteolytic product Aβ. See, e.g., Zohar et al., *Neurobiology of Disease,* 2011, 41: 329-337; Roberts et al., *Lancet,* 1991, 1422-1423; Gentleman e al., *NeuroReport,* 1997, 8: 1519-1522; Iwata et al., *J. Neuropathol Exp. Neurol.,* 2002, 61: 1056-1068. In animal models, the PKC activator Bryostatin-1 was shown to protect against traumatic brain injury-induced learning and memory deficits. See Zohar et al., *Neurobiology of Disease,* 2011, 41: 329-337. Thus, PKC activators may be able to enhance memory and other cognitive functions.

Additionally, some forms of stroke are caused by Aβ, such as those associated with cerebral amyloid angiopathy ("CAA"). See U.S. Patent Application Publication No. 2010/0022645 A1. This disorder is a form of angiopathy in which the same Aβ deposits as found in AD accumulate in the walls of the leptomeninges and superficial cerebral cortical blood vessels of the brain. Amyloid deposition predisposes these blood vessels to failure, increasing the risk of a hemorrhagic stroke. CAA is also associated with transient ischemic attacks, subarachnoid hemorrhage, Down's syndrome, post irradiation necrosis, multiple sclerosis, leucoencephalopathy, spongiform encephalopathy, and dementia pugilistica.

Both PKC-α and PKC-ε are important for synaptogenesis—i.e., the formation of synapses. The high abundance of PKC-ε in presynaptic nerve fibers suggests a role in neurite outgrowth, synaptic formation, and neurotransmitter release. See Shirai et al., *FEBS,* 2008, 29: 1445-1453. Nontoxic drugs activating PKC-α and PKC-ε can promote synaptogensis under non-pathological conditions and actually prevent synaptic loss under pathological conditions. See Nelson et al., *Trends Biochem. Sci.,* 2009, 34: 136-145; Hongpaisan et al., *Proc. Natl. Acad. Sci. USA,* 2007, 104: 19571-19576; Sun et al., *Proc. Natl. Acad. Sci. USA,* 2008, 105: 13620-13625; Sun et al., *Proc. Natl. Acad. Sci. USA,* 2009, 106: 14676-14680.

For example, PKC activators have demonstrated neuroprotective activity in animal models of stroke. See Sun et al., *Eur. J. Pharmacol.,* 2005, 512: 43-51. Several PKC isoforms play a central role in mediating ischemic and reperfusion damage following stroke. Studies with experimental stroke models, mouse genetics, and selective peptide inhibitors and activators have demonstrated that PKC-ε is involved in induction of ischemic tolerance and prevents damage, while PKC-δ and PKC-γ are implicated in injury. See Takayoshi et al., *Stroke,* 2007, 38(2): 375-380; and Bright et al., *Stroke,* 2005; 36: 2781. Postischemic/hypoxic treatment with Bryostatin-1 effectively rescued ischemia-induced deficits in synaptogenesis, neurotrophic activity, and spatial learning and memory. See Sun et al., *Proc. Natl. Acad. Sci. USA.,* 2008, 105(36): 13620-13625.

PKC activation has a crucial role in learning and memory enhancement and PKC activators have been shown to increase memory and learning. See Sun et al., *Eur. J. Pharmacol.* 2005, 512: 43-51; Alkon et al., *Proc. Natl. Acad. Sci. USA.,* 2005, 102: 16432-16437. For example, bryostatin increased the rate of learning in rodents, rabbits, and invertebrates. See Sun et al., *Eur. J. Pharmacol.,* 2005, 512: 43-51; Wang et al., *Behav. Pharmacol.,* 2008, 19: 245-256; and Kuzirian et al., *Biol. Bull.,* 2006, 210: 201-214. Additionally, bryostatin-induced synaptogenesis for long-term associative memory was shown to be regulated by PKC activation. Hongpaisan et al., *Proc. Natl. Acad. Sci. USA,* 2007, 104: 19571-19576.

PKC activation has been associated with a variety of other conditions. For example, PKC activators have demonstrated neuroprotective activity in animal models of depression. See Sun et al., *Eur. J. Pharmacol.,* 2005, 512: 43-51. PKC activators are also associated with prevention and treatment of Parkinson's disease, bipolar disorder, and schizophrenia, mental retardation (and related diseases like autism).

Niemann-Pick disease (NP) refers to a group of inherited metabolic disorders known as lipid storage diseases. Lipids (fatty materials such as waxes, fatty acids, oils, and cholesterol) and proteins are usually broken down into smaller components to provide energy for the body. In Niemann-Pick disease, harmful quantities of lipids accumulate in, for example, the spleen, liver, lungs, bone marrow, and the brain. Symptoms may include lack of muscle coordination, brain degeneration, eye paralysis, learning problems, loss of muscle tone, increased sensitivity to touch, spasticity, feeding and swallowing difficulties, slurred speech, and an enlarged liver and spleen. There may be clouding of the cornea and a characteristic cherry-red halo develops around the center of the retina.

The disease has four related types. Type A, the most severe form, occurs in early infancy. It is characterized by an enlarged liver and spleen, swollen lymph nodes, and profound brain damage by six months of age. Children with this type rarely live beyond 18 months. Type B involves an enlarged liver and spleen, which usually occurs in the pre-teen years. The brain is not affected. In types A and B, insufficient activity of an enzyme called sphingomyelinase causes the buildup of toxic amounts of sphingomyelin, a fatty substance present in every cell of the body. Types C and D may appear early in life or develop in the teen or adult years. Affected individuals have only moderate enlargement of the spleen and liver, but brain damage may be extensive and cause an inability to look up and down, difficulty in walking and swallowing, and progressive loss of vision and hearing. Types C and D are characterized by a defect that disrupts the transport of cholesterol between brain cells. Type D usually occurs in people with an ancestral background in Nova Scotia. Types C and D are caused by a lack of the NPC1 or NPC 2 proteins. NINDS Niemann-Pick Disease Information Page, available at http://www.ninds.nih.gov/disorders/niemann/niemann.htm.

It has been reported that the intermediate filament vimentin is hypophosphorylated in Niemann-Pick Diseased cells compared to Wt cells and that this hypophosphorylation results from reduced PKC activity, in particular the α, ε, and βII isoforms. Increased PKC α, ε, and/or βII expression can increase levels of soluble vimentin in Niemann-Pick Diseased cells, ameliorating the transport block of LDL-derived cholesterol from their lysosomes to the endoplasmic reticulum for esterification. Tamari et al., *PKC Activation in Niemann Pick C1 Cells Restores Subcellular Cholesterol Transport*, PLOS ONE, Vol. 8, Iss. 8 (2013).

PKC activators can be broad-spectrum activators, acting on multiple isoforms of PKC, or can be selective for certain isoforms. While all types of PKC activators are of interest, selective PKC activators may offer unique advantages because different isoforms perform different, and sometimes opposite, functions. For example, PKC-δ and PKC-θ are often regarded as having a pro-apoptotic function because they are components of the caspase apoptosis pathway. PKC-ε, by contrast, has an opposite role: its activation promotes proliferation and cell survival, and inhibits apoptosis. See Nelson et al., *Trends in Biochemical Sciences*, 2009, 34(3): 136-145.

PKC-ε activators have been shown in numerous animal models, as discussed above, to have neuroprotective activity and would be useful therapeutic agents against a multitude of neurological diseases, conditions, or disorders, including, but not limited to, Alzheimer's disease, schizophrenia, depression, and stroke.

Polyunsaturated fatty acids ("PUFAs"), such as arachidonic acid and 2-hydroxy-9-cis-octadecenoic acid (i.e., minerval), and monounsaturated fatty acids ("MUFAs") are known PKC-ε activators. PUFAs and MUFAs are interesting molecules in that they are essential components of the nervous system. They are known to increase membrane fluidity, rapidly oxidize to highly bioactive products, produce a variety of inflammatory and hormonal effects, and are rapidly degraded and metabolized. In addition, they are of low molecular weight and are able to cross the blood-brain barrier. Further, PUFAs and MUFAs are stable to acid and base, making them potentially effective for oral administration.

Like PUFAs and MUFAs, certain derivatives of PUFAs and MUFAs have been shown to be PKC-ε activators. For example, cyclopropanated PUFAs such as DCPLA methyl ester (i.e., linoleic acid derivative), AA-CP4 methyl ester (i.e., arachidonic acid derivative), DHA-CP6 methyl ester (i.e., docosahexaenoic acid derivative), and EPA-CP5 methyl ester (i.e., eicosapentaenoic acid derivative) may be able to selectively activate PKC-ε. See *Journal of Biological Chemistry*, 2009, 284(50): 34514-34521; see also U.S. Patent Application Publication No. 2010/0022645 A1; International Application Publication No. WO 2013/071281.

Potency, for example, is part of the criteria in determining the utility of a drug for treating neurological disorders. A highly potent drug implies that the desired effects may be achieved at lower doses as compared to the required dose of a less potent drug. Thus, a highly potent drug administered at lower doses may result in fewer side effects because of, e.g., nonspecific binding to other targets, and higher brain specificity. Many known PKC-ε activators, however, suffer from several disadvantages, including low specificity and/or low potency.

The present disclosure is directed to new chemical entities that possess high potency and specificity for PKC-ε. More specifically, these new chemical entities are halogenated esters of unsaturated fatty acids or derivatives thereof. As potent, specific activators of PKC-ε, the halogenated esters disclosed herein may be suited for use as therapeutic agents against neurological diseases, conditions, and disorders, such as Alzheimer's disease and other neurodegenerative diseases.

In one aspect, the present disclosure includes a compound chosen from a halogenated ester of a polyunsaturated fatty acid, monounsaturated fatty acid, or derivative thereof. In a further aspect, there is disclosed a halogenated ester of 8-[2-(2-pentylcyclopropylmethyl)-cyclopropyl]-octanoic acid (DCPLA).

In another aspect, the present disclosure includes a composition comprising at least one halogenated ester of a polyunsaturated fatty acid, monounsaturated fatty acid, or derivative thereof, and a pharmaceutically acceptable carrier. In a further aspect, there is disclosed a composition comprising a halogenated ester of DCPLA and a pharmaceutically acceptable carrier.

In yet another aspect, the present disclosure includes a method for treating one or more diseases, conditions, and disorders, comprising administering to a patient in need thereof an effective amount of at least one halogenated ester of a polyunsaturated fatty acid, monounsaturated fatty acid, or derivative thereof, wherein the diseases, conditions and disorders are neurodegenerative diseases or conditions, neuroaffective disorders, stroke, mental retardation, and brain injury. In a further aspect, there is disclosed a method for treating one or more diseases, conditions, and disorders, comprising administering to a patient in need thereof an effective amount of a halogenated ester of DCPLA, wherein the diseases, conditions and disorders are neurodegenerative diseases or conditions, neuroaffective disorders, stroke, mental retardation, and brain injury.

In a further aspect, the present disclosure includes using the halogenated esters described herein as positron emission tomography (PET) agents for in vivo imaging of PKC levels, and hence neurological function.

DESCRIPTION

Figure 1:
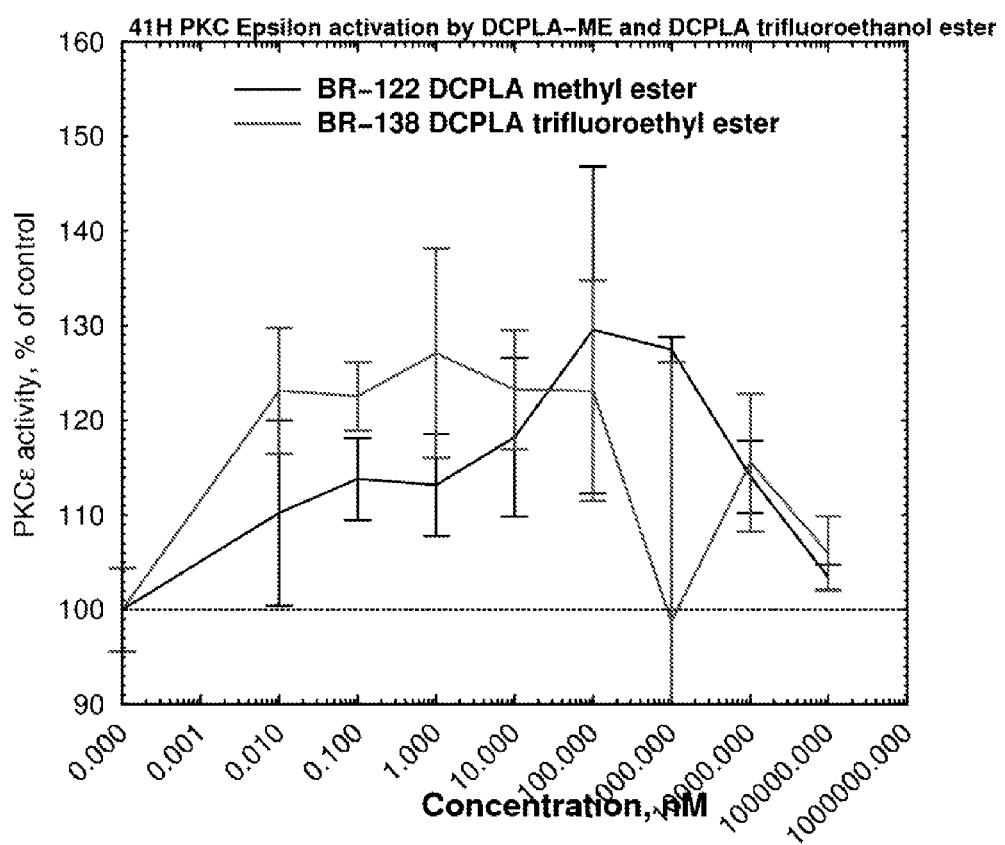
FIG. 1 shows PKC-ε activation by DCPLA-EtF3 versus DCPLA methyl ester.

As used herein, the singular forms "a," "an," and "the" include plural reference unless the context dictates otherwise.

As used herein, "protein kinase C activator" or "PKC activator", or specifically "PKC-ε activator," refers to a substance that increases the rate of the reaction catalyzed by protein kinase C, or specifically PKC-ε, by binding to the protein kinase C, or specifically PKC-ε. As used herein, "selective activation" means activation of one PKC isozyme, e.g., PKC-ε, to a greater detectable extent than another PKC isozyme.

As used herein, the term "fatty acid" refers to a compound composed of a hydrocarbon chain and ending in free acid.

Fatty acids may be saturated or unsaturated, branched or unbranched, and naturally-occurring or synthetic. Linoleic acid is an example of a fatty acid (shown below in the free acid form).

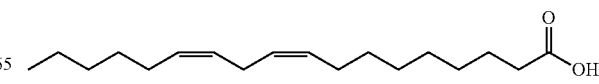

An "unsaturated fatty acid" is a fatty acid that contains at least one carbon-carbon double bond within the hydrocarbon chain. Each double bond can be in cis or trans form.

A "monounsaturated fatty acid" or "MUFA" contains one carbon-carbon double bond. Oleic acid is an example of a monounsaturated fatty acid. A "polyunsaturated fatty acid"

one to six cyclopropane rings. Shown below are the CP1 and CP6 forms. With respect to compounds that are not completely cyclopropanated (e.g. DHA-CP1), the cyclopropane group(s) can occur at any of the carbon-carbon double bonds.

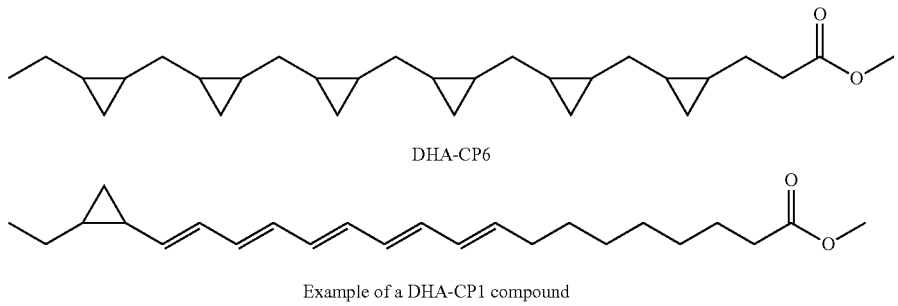

Example of a DHA-CP1 compound or "PUFA" contains more than one carbon-carbon double bonds. Linoleic acid is an example of a polyunsaturated fatty acid.

As used herein, the term "cyclopropanated" or "CP" refers to a compound wherein at least one carbon-carbon double bond in the molecule has been replaced with a cyclopropane group. The cyclopropyl group may be in cis or trans configuration. Unless otherwise indicated, it should be understood that the cyclopropyl group is in the cis configuration.

The terms "cyclopropanated monounsaturated fatty acid" or "cyclopropanated MUFA" therefore refer to compounds wherein the carbon-carbon double bond is replaced by a cyclopropyl group. An example of a cyclopropanated MUFA is 8-(2-octylcyclopropyl)octanoic acid (shown below in free acid form).

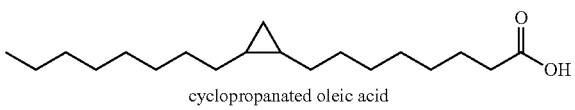 [SMILES: CCCCCCCCC1CC1CCCCCCCC(=O)O]

cyclopropanated oleic acid

Similarly, the terms "cyclopropanated polyunsaturated fatty acid" or "cyclopropanated PUFA" refer to compounds wherein at least one of the carbon-carbon double bonds in the polyunsaturated fatty acid is replaced by a cyclopropyl group. An example of a cyclopropanated PUFA is 8-[2-(2-pentylcyclopropylmethyl)-cyclopropyl]-octanoic acid ("DCPLA") (shown below in the free acid form).

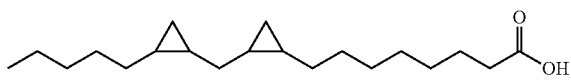

Compounds with multiple carbon-carbon double bonds have many cyclopropanated forms. For example, a polyunsaturated compound in which only one double bond has been cyclopropanated would be said to be in "CP1 form." Similarly, "CP6 form" indicates that six double bonds are cyclopropanated.

For example, docosahexaenoic acid ("DHA") methyl ester has six carbon-carbon double bonds and thus can have Esters of unsaturated fatty acids can be prepared according to techniques known in the art. See, e.g., *Journal of Biological Chemistry*, 2009, 284(50): 34514-34521. For example, linoleic acid can be esterified using $SOCl_2$ in methanol and pyridine. The subsequent ester can then be cyclopropanated using a modified Simmons-Smith reaction with chloroiodomethane and diethylzinc. Those skilled in the art understand that certain expressions are interchangeable. For example, "methyl ester of DCPLA" is the same as "DCPLA methyl ester," which is the same as "DCPLA in the methyl ester form."

Linoleic acid and esters thereof are generally commercially available. Alternatively, the acids and esters may be isolated from natural sources (e.g., vegetable oil) or synthesized (e.g., by chemical reactions). Esterification of linoleic acid can be performed according to known methods. For example, linoleic acid can be esterified with an alcohol in the presence of an acid.

As used herein, the term "halogenated group" means a chemical group having at least one hydrogen replaced with a halogen, such as fluorine, chlorine, bromine, etc.

As used herein, the term "halogenated ester" means an ester wherein the alkoxy or aryloxy group of the ester has at least one hydrogen replaced with a halogen, such as fluorine, chlorine, bromine, etc. The alkoxy or aryloxy group may contain more than one halogen. For example, the halogenated ester may be monofluoro, di-fluoro, tri-fluoro, tetra-fluoro, etc.

PUFAs are essential components of the nervous system and have numerous health benefits. In general, PUFAs increase membrane fluidity, rapidly oxidize to highly bioactive products, produce a variety of inflammatory and hormonal effects, and are rapidly degraded and metabolized. The inflammatory effects and rapid metabolism is likely the result of their active carbon-carbon double bonds. These compounds may be potent activators of PKC, most likely by binding the PS site.

One class of PKC-ε activating fatty acids is Omega-3 PUFAs. In one embodiment, the Omega-3 PUFAs are chosen from docosahexaenoic acid, eicosapentaenoic acid, rumelenic acid, parinaric acid, and linolenic acid.

Another class of PKC-ε activating fatty acids is Omega-6 PUFAs. In one embodiment, the Omega-6 PUFAs are chosen from linoleic acid, arachidonic acid, eicosadienoic acid, dihomo-gamma-linolenic acid, docosadienoic acid, adrenic acid, calendic acid, docosapentaenoic acid, jacaric acid, pinolenic acid, podocarpic acid, tetracosatetraenoic acid, and tetracosapentaenoic acid.

Another class of PKC-ε activating fatty acids is Omega-9 PUFAs. In one embodiment, the Omega-9 PUFA derivatives are chosen from eicosenoic acid, mead acid, erucic acid, and nervonic acid.

An additional class of PKC-ε activating fatty acids is Omega-5 and Omega-7 PUFAs. In one embodiment, the Omega-5 and Omega-7 PUFA derivatives are chosen from rumenic acid, alpha-elostearic acid, catalpic acid, and punicic acid.

Yet another class of PKC-ε activating fatty acids is monounsaturated fatty acids ("MUFAs"). In one embodiment, the MUFAs are chosen from oleic acid and elaidic acid.

A further class of PKC-ε activating fatty acids is PUFA and MUFA derivatives, and cyclopropanated derivatives in particular. Like their parent molecules, PUFA derivatives are thought to activate PKC-ε by binding to the PS site. Cyclopropanated fatty acids exhibit low toxicity and are readily imported into the brain where they exhibit a long half-life ($t_{1/2}$). Conversion of the double bonds into cyclopropane rings prevents oxidation and metabolism to inflammatory byproducts and creates a more rigid U-shaped 3D structure that may result in greater PKC activation. Moreover, this U-shape may result in greater isoform specificity. For example, cyclopropanated fatty acids may exhibit potent and selective activation of PKC-ε.

The Simmons-Smith cyclopropanation reaction is an efficient way of converting double bonds to cyclopropane groups. This reaction, acting through a carbenoid intermediate, preserves the cis-stereochemistry of the parent molecule. Thus, the PKC-activating properties are increased while metabolism into other molecules like bioreactive eicosanoids, thromboxanes, or prostaglandins is prevented.

PUFA and MUFA derivatives include, for example, cyclopropanated derivatives of the fatty acids described above. In one embodiment, the Omega-3 PUFA derivatives are chosen from cyclopropanated docosahexaenoic acid, cyclopropanated eicosapentaenoic acid, cyclopropanated rumelenic acid, cyclopropanated parinaric acid, and cyclopropanated linolenic acid (CP3 form shown below).

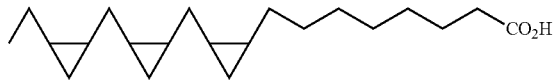

In another embodiment, the Omega-6 PUFA derivatives are chosen from cyclopropanated linoleic acid ("DCPLA," CP2 form shown below),

cyclopropanated arachidonic acid, cyclopropanated eicosadienoic acid, cyclopropanated dihomo-gamma-linolenic acid, cyclopropanated docosadienoic acid, cyclopropanated adrenic acid, cyclopropanated calendic acid, cyclopropanated docosapentaenoic acid, cyclopropanated jacaric acid, cyclopropanated pinolenic acid, cyclopropanated podocarpic acid, cyclopropanated tetracosatetraenoic acid, and cyclopropanated tetracosapentaenoic acid.

Vernolic acid is a naturally occurring compound. However, it is an epoxyl derivative of linoleic acid and therefore, as used herein, is considered an Omega-6 PUFA derivative. In addition to vernolic acid, cyclopropanated vernolic acid (shown below) is an Omega-6 PUFA derivative.

In another embodiment, the Omega-9 PUFA derivatives are chosen from cyclopropanated eicosenoic acid, cyclopropanated mead acid, cyclopropanated erucic acid, and cyclopropanated nervonic acid.

In a further embodiment, the Omega-5 and Omega-7 PUFA derivatives are chosen from cyclopropanated rumenic acid, cyclopropanated alpha-elostearic acid, cyclopropanated catalpic acid, and cyclopropanated punicic acid.

In a further embodiment, the MUFA derivatives are chosen from cyclopropanated oleic acid (shown below),

and cyclopropanated elaidic acid (shown below).

PKC-ε activating MUFA derivatives include epoxylated compounds such as trans-9,10-epoxystearic acid (shown below).

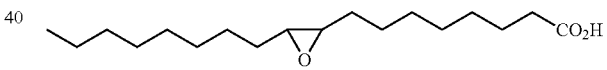

The present disclosure is directed to halogenated esters of PUFAs and MUFAs, as well as to halogenated esters of PUFA and MUFA derivatives, including, but not limited to, halogenated esters of the PUFAs, MUFAs, and derivatives thereof described above. The present disclosure includes the discovery that halogenated esters of PUFAs, MUFAs and derivatives thereof may activate PKC, and PKC-ε in particular. The halogenated esters may be even more selective and/or more potent PKC-ε activators than both the corresponding acid form and the ester form absent halogenation.

In one embodiment, the halogenated ester of a PUFA, MUFA, or derivative thereof may be fluorinated, chlorinated, brominated, iodinated, or combinations thereof. In certain embodiments, the halogenated ester is a fluorinated ester.

In one embodiment, the halogenated ester is chosen from halogenated alkyl esters. The alkyl group of the halogenated alkyl esters may be linear, branched, and/or cyclic. The alkyl groups may be saturated or unsaturated. If the alkyl group is unsaturated, it may be cyclopropanated.

The alkyl group of the halogenated alkyl esters may be halogenated (1) by substituting a halogen for at least one hydrogen in the linear, branched, or cyclic alkyl group (examples shown below); (2) by substituting a functional group, e.g., an aryl group, for at least one hydrogen in the linear, branched, or cyclic alkyl group, wherein the functional group is substituted with a halogen and/or halogenated group (examples shown below); or (3) by a combination of (1) and (2) (examples shown below).

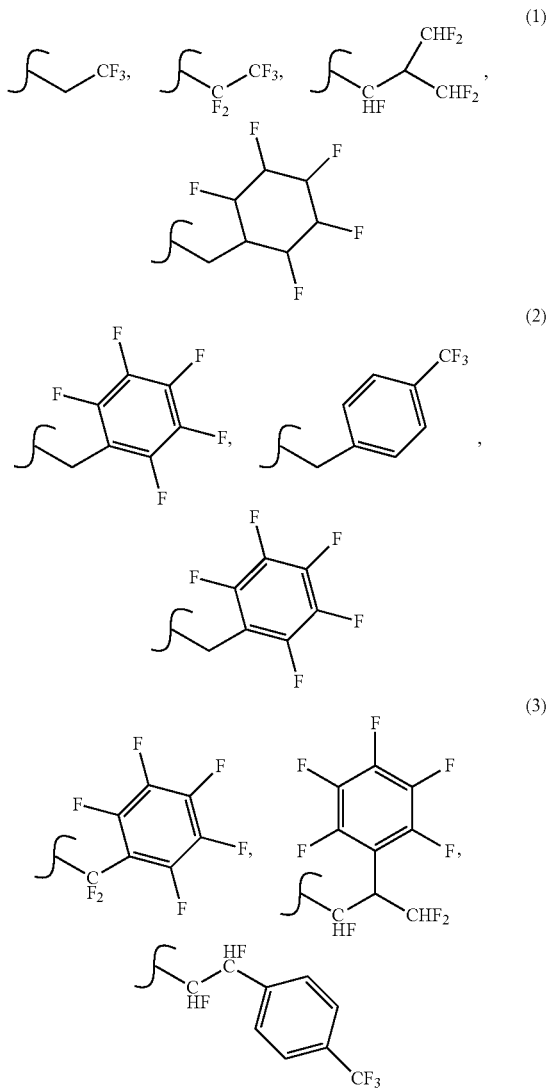

In one embodiment, aside from substituting any halogens for at least one hydrogen in the linear, branched, or cyclic alkyl group, the alkyl group may be further substituted with one or more functional groups, such as an aryl group, a hydroxyl group, an ether group, and/or a carboxyl group. An example of an aryl-substituted alkyl group is benzyl. The at least one functional group may itself be substituted, e.g., with a halogen or halogenated group as discussed above. An example of an aryl functional group that is substituted with a halogenated group is (trifluoromethyl)phenyl (see (2) above).

In one embodiment, the halogenated alkyl ester is chosen from halogenated methyl ester, ethyl ester, isopropyl ester, tert-butyl ester, and benzyl ester. In one embodiment, the halogenated ester is a fluorinated alkyl ester. In a further embodiment, the halogenated ester is a trifluoroalkyl ester.

In one embodiment, the halogenated alkyl ester is prepared using a halogenated linear, branched, or cyclic alkyl alcohol. An example of a halogenated linear alcohol is 2,2,2,-trifluoroethanol. An example of a halogenated branched alkyl alcohol is 1,1,1-trifluoro-2-propanol. An example of a halogenated cyclic alkyl alcohol is 2,3,4,5,6-pentafluorocyclohexanol. In another embodiment, the halogenated alkyl ester is prepared using a halogenated benzyl alcohol, such as 4-(trifluoromethyl)benzyl alcohol.

In another embodiment, the halogenated ester is chosen from halogenated aryl esters. The aryl group of the halogenated aryl esters may be monocyclic or multicyclic.

The aryl group of the halogenated aryl esters may be halogenated (1) by substituting a halogen for at least one hydrogen in the aryl group (examples shown below); (2) by substituting a functional group, e.g., an alkyl group, for at least one hydrogen in the aryl group, wherein the functional group is substituted with a halogen and/or halogenated group (examples shown below); or (3) by a combination of (1) and (2) (examples shown below).

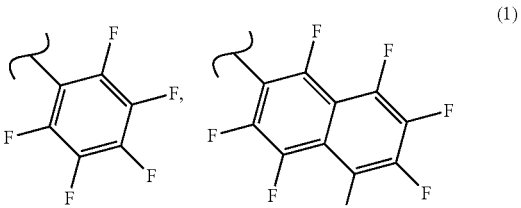

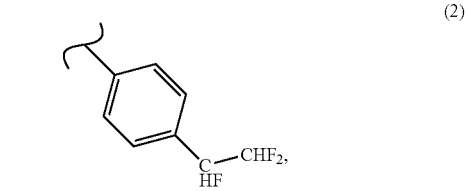

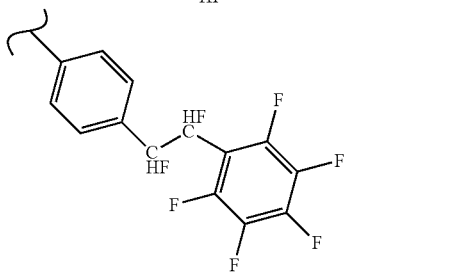

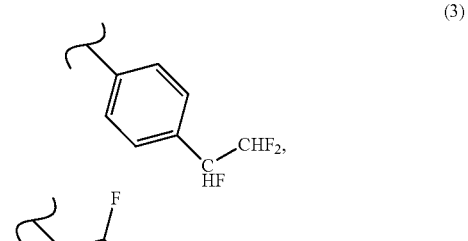

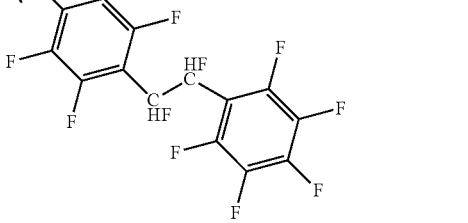

In one embodiment, aside from substituting any halogens for at least one hydrogen in the aryl group, the aryl group may be further substituted with one or more functional groups, such as an alkyl group, a hydroxyl group, an ether group, and/or a carboxyl group. The at least one functional group may itself be substituted, e.g., with a halogen or halogenated group as discussed above.

In one embodiment, the halogenated ester is a fluorinated aryl ester.

In one embodiment, the halogenated aryl ester is prepared using a halogenated aromatic alcohol. An example of a halogenated aromatic alcohol is 2,3,4,5,6-pentafluorophenol.

In a particular embodiment, the present disclosure includes a halogenated ester of 8-[2-(2-pentylcyclopropylmethyl)-cyclopropyl]-octanoic acid ("DCPLA") (shown below in the free acid form).

In one embodiment, the halogenated ester of DCPLA may be fluorinated, chlorinated, brominated, iodinated, or combinations thereof. In certain embodiments, the halogenated ester of DCPLA is a fluorinated ester.

In one embodiment, the halogenated ester of DCPLA is a halogenated alkyl ester. In another embodiment, the halogenated ester of DCPLA is a halogenated aryl ester. In some embodiments, the alkyl groups of the halogenated alkyl esters and the aryl groups of the halogenated aryl esters are chosen as described above.

In one embodiment, the halogenated ester of DCPLA is chosen from halogenated methyl ester, ethyl ester, isopropyl ester, tert-butyl ester, and benzyl ester.

In one embodiment, the halogenated ester of DCPLA is a fluorinated alkyl ester. In a further embodiment, the halogenated ester of DCPLA is a trifluoroalkyl ester. In a further embodiment, the halogenated ester of DCPLA is chosen from least one halogenated ester of a PUFA, MUFA, or derivative thereof, and a pharmaceutically acceptable carrier. The at least one halogenated ester may be a halogenated ester as described herein.

For example, in one embodiment, the PUFA is chosen from linoleic acid, arachidonic acid, eicosadienoic acid, dihomo-gamma-linolenic acid, docosadienoic acid, adrenic acid, calendic acid, docosapentaenoic acid, jacaric acid, pinolenic acid, podocarpic acid, tetracosatetraenoic acid, tetracosapentaenoic acid, vernolic acid, docosahexaenoic acid, eicosapentaenoic acid, rumelenic acid, parinaric acid, linolenic acid, eicosenoic acid, mead acid, erucic acid, nervonic acid, rumenic acid, alpha-elostearic acid, catalpic acid, and punicic acid and MUFAs may be cyclopropanated.

In one embodiment, the MUFA is chosen from oleic acid and elaidic acid.

In another embodiment, the PUFA, MUFA, or derivative thereof is a cyclopropanated PUFA or MUFA, as described herein.

In one embodiment, the halogenated ester for use in the disclosed compositions is a fluorinated ester. In one embodiment, the halogenated ester for use in the disclosed compositions is a halogenated alkyl ester, as described herein. In another embodiment, the halogenated ester is a halogenated aryl ester, as described herein. In a further embodiment, the halogenated ester is a fluorinated alkyl ester.

In a particular embodiment, the present disclosure includes a composition comprising at least one halogenated ester of DCPLA and a pharmaceutically acceptable carrier. The halogenated ester of DCPLA for use in the presently disclosed composition may be chosen as described herein.

For example, the halogenated ester of DCPLA for use in the disclosed compositions may be a fluorinated ester. In one embodiment, the halogenated ester of DCPLA is a halogenated alkyl ester, as described herein. In another embodiment, the halogenated ester is a halogenated aryl ester, as described herein. In a further embodiment, the halogenated ester of DCPLA for use in the disclosed compositions is a fluorinated alkyl ester. In a further embodiment, the halo-

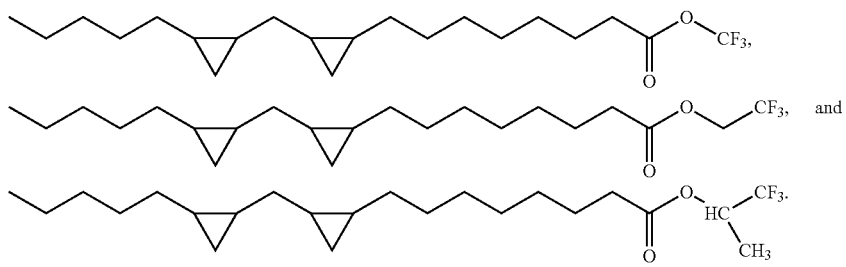

The present disclosure also includes compositions comprising at least one PKC-ε activator. For example, the present disclosure includes a composition comprising at least one halogenated ester of DCPLA is a trifluoroalkyl ester. In a further embodiment, the halogenated ester of DCPLA is chosen from

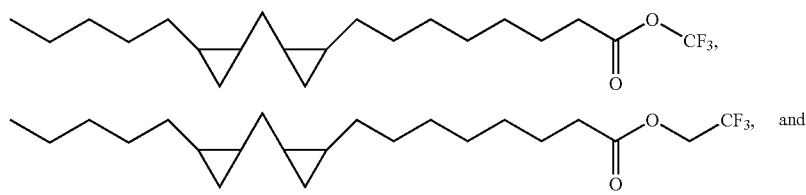

-continued

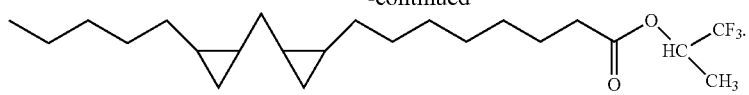

The formulations of the compositions described herein may be prepared by any suitable method known in the art of pharmacology. In general, such preparatory methods include bringing the active ingredient into association with a carrier or one or more other accessory ingredients, then, if necessary or desirable, shaping or packaging the product into a desired single- or multi-dose unit.

Although the descriptions of pharmaceutical compositions provided herein are principally directed to pharmaceutical compositions suitable for ethical administration to humans, it will be understood by a skilled artisan that such compositions are generally suitable for administration to animals of all sorts. Modification of pharmaceutical compositions suitable for administration to humans or to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure are contemplated include, but are not limited to, humans and other primates, and other mammals.

In one embodiment, the compositions disclosed herein may be formulated with a pharmaceutically acceptable carrier for administration. Pharmaceutically acceptable carriers include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other additional ingredients that may be included in the pharmaceutical compositions of the disclosure are generally known in the art and may be described, for example, in *Remington's Pharmaceutical Sciences*, Genaro, ed., Mack Publishing Co., Easton, Pa., 1985, and *Remington's Pharmaceutical Sciences*, 20th Ed., Mack Publishing Co. 2000, both incorporated by reference herein.

In one embodiment, the carrier is an aqueous or hydrophilic carrier. In a further embodiment, the carrier can be water, saline, or dimethylsulfoxide. In another embodiment, the carrier is a hydrophobic carrier. Hydrophobic carriers include inclusion complexes, dispersions (such as micelles, microemulsions, and emulsions), and liposomes. Exemplary hydrophobic carriers include inclusion complexes, micelles, and liposomes. See, e.g., Remington's: The Science and Practice of Pharmacy 20th ed., ed. Gennaro, Lippincott: Philadelphia, Pa. 2003, incorporated by reference herein. In addition, other compounds may be included either in the hydrophobic carrier or the solution, e.g., to stabilize the formulation.

The compositions disclosed herein may be administrated by any suitable route including oral, parenteral, transmucosal, intranasal, inhalation, or transdermal routes. Parenteral routes include intravenous, intra-arteriolar, intramuscular, intradermal, subcutaneous, intraperitoneal, intraventricular, intrathecal, and intracranial administration. A suitable route of administration may be chosen to permit crossing the blood-brain barrier. See e.g., *J. Lipid Res.* (2001) vol. 42, pp. 678-685, incorporated by reference herein.

In one embodiment, the compositions described herein may be formulated in oral dosage forms. For oral administration, the composition may take the form of a tablet or capsule prepared by conventional means with, for example, carriers such as binding agents (e.g., pregelatinized maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods generally known in the art.

In another embodiment, the compositions herein are formulated into a liquid preparation. Such preparations may take the form of, for example, solutions, syrups or suspensions, or they may be presented as a dry product for constitution with water or other suitable vehicle before use. Such liquid preparations may be prepared by conventional means with, for examples, pharmaceutically acceptable carriers such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl p-hydroxybenzoates, or sorbic acid). The preparations may also comprise buffer salts, flavoring, coloring, and sweetening agents as appropriate. In one embodiment, the liquid preparation is for oral administration.

In another embodiment of the present disclosure, the compositions herein may be formulated for parenteral administration such as bolus injection or continuous infusion. Formulations for injection may be presented in unit dosage form, e.g., in ampoules, or in multi-dose containers, with an added preservative. The compositions may take such forms as suspensions, solutions, dispersions, or emulsions in oily or aqueous vehicles, and may contain formulatory agents such as suspending, stabilizing, and/or dispersing agents.

In another embodiment, the compositions herein may be formulated as depot preparations. Such formulations may be administered by implantation (for example, subcutaneously or intramuscularly) or by intramuscular injection. For example, the compositions may be formulated with a suitable polymeric or hydrophobic material (for example, as an emulsion in an acceptable oil) or ion exchange resin, or as a sparingly soluble derivative, for example, as a sparingly soluble salt.

In another embodiment, at least one halogenated ester of a PUFA, MUFA, or derivative thereof may be delivered in a vesicle, such as a micelle, liposome, or an artificial low-density lipoprotein (LDL) particle. See, e.g., U.S. Pat. No. 7,682,627.

In one embodiment, the at least one halogenated ester of a PUFA, MUFA, or derivative thereof, such as at least one halogenated ester of DCPLA, is present in the disclosed compositions in an amount effective for one or more of the following: improving learning, improving memory, reducing β-amyloid levels, treating a disease associated with synaptic loss or synaptic damage, treating one or more neurodegenerative diseases or conditions, treating one or more neuroaffective disorders, treating stroke, treating mental retardation, and treating brain injury.

In one embodiment, the neurodegenerative diseases or conditions are Alzheimer's disease, Parkinson's disease, Fragile X, Niemann-Pick (e.g., Niemann-Pick C), and dementia conditions (e.g., Parkinson's dementia, frontotemporal dementia, and vascular dementia). In one embodiment, the neuroaffective disorders are depression, bipolar disorder, schizophrenia, and Post-Traumatic Stress Disorder (PTSD).

In one embodiment, the halogenated ester or esters may be present in the compositions described herein in an amount ranging from about 0.01% to about 100%, from about 0.1% to about 90%, from about 0.1% to about 60%, from about 0.1% to about 30% by weight, or from about 1% to about 10% by weight of the final composition. In another embodiment, the halogenated ester or esters may be present in the composition in an amount ranging from about 0.01% to about 100%, from about 0.1% to about 95%, from about 1% to about 90%, from about 5% to about 85%, from about 10% to about 80%, and from about 25% to about 75%, by weight of the final composition.

The present disclosure further includes kits that may be utilized for preparing and/or for administering to a subject pharmaceutical compositions of at least one halogenated ester described herein.

The kits may comprise devices for storage and/or administration. For example, the kits may comprise syringe(s), needle(s), needle-less injection device(s), sterile pad(s), swab(s), vial(s), ampoule(s), cartridge(s), bottle(s), and the like. The storage and/or administration devices may be graduated to allow, for example, measuring volumes. In one embodiment, the devices, syringes, ampules, cartridges, bottles or other such vessels for storing and/or subsequently mixing the compositions of at least one halogenated ester disclosed herein may, or may not have more than one chamber.

In a further embodiment, the kits may comprise pharmaceutical compositions of at least one halogenated ester described herein stored within the same or separate ampules, vials, syringes, cartridges, bottles, or other such vessels from other components in the system. The kits may also include additional buffers, needles, needle-less injection devices, sterile pads, or swabs.

The kits may also comprise one or more anesthetics, such as local anesthetics. In one embodiment, the anesthetics are in a ready-to-use formulation, for example an injectable formulation (optionally in one or more pre-loaded syringes), or a formulation that may be applied topically. Topical formulations of anesthetics may be in the form of an anesthetic applied to a pad, swab, towelette, disposable napkin, cloth, patch, bandage, gauze, cotton ball, Q-tip™, ointment, cream, gel, paste, liquid, or any other topically applied formulation. Anesthetics for use with the present disclosure may include, but are not limited to lidocaine, marcaine, cocaine, and xylocaine.

The kits may also contain instructions relating to the use of the pharmaceutical compositions of at least one halogenated ester described herein and procedures for mixing, diluting, or combining formulations of at least one halogenated ester. The instructions may also contain directions for properly diluting a formulation of at least one halogenated ester described herein to obtain a desired pH or range of pHs and/or a desired specific activity and/or protein concentration after mixing but prior to administration. The instructions may also contain dosing information. The instructions may also contain material directed to methods for selecting subjects for treatment with the disclosed pharmaceutical compositions of at least one halogenated ester of a PUFA, MUFA, or derivative thereof, as disclosed herein.

The present disclosure also relates to methods of treatment using at least one halogenated ester of a PUFA, MUFA, or derivative thereof as described herein. For example, the present disclosure provides for a method for improving learning, comprising administering to a patient in need thereof an effective amount of at least one halogenated ester of a PUFA, MUFA, or derivative thereof. In another embodiment, the present disclosure includes methods for improving memory, comprising administering to a patient in need thereof an effective amount of at least one halogenated ester of a PUFA, MUFA, or derivative thereof.

In another embodiment, the present disclosure provides for a method for reducing β-amyloid levels, comprising administering to a patient in need thereof an effective amount of at least one halogenated ester of a PUFA, MUFA, or derivative thereof. The present disclosure further includes a method for treating a disease associated with synaptic loss or synaptic damage, comprising administering to a patient in need thereof an effective amount of at least one halogenated ester of a PUFA, MUFA, or derivative thereof.

The present disclosure further includes a method for treating one or more diseases, conditions, and disorders, comprising administering to a patient in need thereof an effective amount of at least one halogenated ester of a PUFA, MUFA, or derivative thereof, wherein the diseases, conditions, and disorders are neurodegenerative diseases or conditions, neuroaffective disorders, stroke, mental retardation, and brain injury. In one embodiment, the neurodegenerative diseases or conditions are Alzheimer's disease, Parkinson's disease, Fragile X, Niemann-Pick (e.g., Niemann-Pick C), and dementia conditions (e.g., Parkinson's dementia, frontotemporal dementia, and vascular dementia). In one embodiment, the neuroaffective disorders are depression, bipolar disorder, schizophrenia, and Post-Traumatic Stress Disorder (PTSD). The neurodegenerative diseases or conditions may be caused by, for example, exposure to at least one neurotoxic chemical such as a heavy metal. The brain injury may be traumatic brain injury or brain injury induced by irradiation.

In another embodiment, the present disclosure provides a method for treating ischemia and/or hypoxia as a result of open-heart surgery comprising administering to a patient in need thereof at least one halogenated ester of a PUFA, MUFA, or derivative thereof, with administration being before or after surgery.

In some embodiments, the at least one halogenated ester of a PUFA, MUFA, or derivative thereof is administered as a composition described herein. The halogenated esters may be administered by conventional methods such as oral, parenteral, transmucosal, intranasal, inhalation, or transdermal administration. Parenteral administration includes intravenous, intra-arteriolar, intramuscular, intradermal, subcutaneous, intraperitoneal, intraventricular, intrathecal, and intracranial administration.

In a further embodiment, the doses for administration may suitably be prepared so as to deliver from about 1 mg to about 10 g, such as from about 5 mg to about 5 g, from about 50 mg to about 2 g, from about 100 mg to about 1.5 g, from about 150 mg to about 1 g, or from about 250 mg to about 500 mg of at least one halogenated ester of a PUFA, MUFA, or derivative thereof, such as a halogenated ester of DCPLA.

The at least one halogenated ester of a PUFA, MUFA, or derivative thereof for use in the disclosed methods may be a halogenated ester as described herein.

A further aspect of the disclosure is the use of at least one ester of a PUFA, MUFA, or derivative thereof in the preparation of a medicament for improving learning, for improving memory, for reducing β-amyloid levels, for treating a disease associated with synaptic loss or synaptic damage, for treating neurodegenerative diseases or conditions, for treating neuroaffective disorders, for treating depression, for treating stroke, and for treating brain injuries.

Another aspect of the present disclosure includes using the halogenated esters as described herein as positron emission tomography (PET) agents for in vivo imaging of PKC levels and hence neurological function, such as memory acquisition. For example, in this aspect, the present disclosure includes halogenated esters as described herein, and the compositions and methods of using the same, wherein at least one halogen in the halogenated ester is a radioactive halogen or radioactive halogen isotope. Radioactive halogen isotope $^{18}F$, for example, undergoes spontaneous nuclear decay by emission of a positron. The $^{18}F$ isotope has a half-life of 110 minutes, and is commonly used in PET scanning.

Thus, there is disclosed a method for imaging PKC levels in the brain of a subject comprising administering to the subject an effective amount of at least one halogenated ester as described herein, wherein at least one halogen in the halogenated ester contains at least one radioactive halogen or radioactive halogen isotope. In one embodiment, at least one halogen in the halogenated ester is $^{18}F$ isotope.

There is also disclosed a method for monitoring neurological function in a subject comprising administering to the subject an effective amount of at least one halogenated ester as described herein, wherein at least one halogen in the halogenated ester contains at least one radioactive halogen or radioactive halogen isotope. In one embodiment, at least one halogen in the halogenated ester is $^{18}F$ isotope. In one embodiment, the brain function is memory acquisition.

The compounds, compositions, kits, and methods described herein will be further described by the following examples.

EXAMPLES

All numbers used herein are to be understood as being modified by the term "about."

PUFAs and MUFAs are generally commercially available and cyclopropanation of these compounds is known in the art. See, e.g., Nelson et al. (2009) *J Biol Chem* 274, 34514-34521. Esters can be prepared as known in the art—e.g., through esterification of an alcohol and a carboxylic acid. For alcohols that are unstable in acid, enzymes can be used to perform the esterification.

Example 1: Synthesis of DCPLA-trifluoroethyl Ester (DCPLA-EtF3)

DCPLA-EtF3 was prepared by base transesterification. Two grams of DCPLA methyl ester were mixed with 0.5 grams of KOH, 2 grams of molecular sieves, and 10 ml of 2,2,2-trifluoroethanol in a round-bottom flask. The mixture was refluxed for 2 hours and tested for formation of product by silica gel TLC using as a solvent 10% ethyl acetate in hexane. The reaction was stopped by addition of 20 ml hexane, 1 ml acetic acid, and 10 ml water. The product was extracted into hexane, washed with water, and evaporated. The product was then isolated by preparative silica gel TLC using 10% ethyl acetate in hexane.

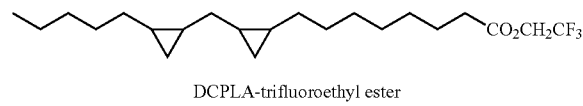

DCPLA-trifluoroethyl ester

Example 2: Synthesis of DCPLA-trifluoromethyl Ester (DCPLA-MeF3)

DCPLA methyl ester (50 μl) was mixed with 1 ml trifluoroethanol, 30 mg TBD (1,5,7-triazabicyclo[4.4.0]dec-5-ene) and 0.2 g molecular sieves in a 10 ml ReactiVial. The mixture was reacted in an incubator for 3 days at 70° C. Then 0.2 ml glacial acetic acid, 2 ml chloroform, and 5 ml water were added. The mixture was vortexed to extract and centrifuged. The organic phase was washed with 5 ml water and the product (49.97 mg) was evaporated to dryness.

DCPLA-trifluoromethyl ester

Example 3: Synthesis of 1,1,1-trifluoropropan-2-yl DCPLA

DCPLA methyl ester (30 μl) was mixed with 1 ml 1,1,1-trifluoro-2-propanol, 30 mg TBD (1,5,7-triazabicyclo[4.4.0]dec-5-ene) and 0.2 g molecular sieves in a 10 ml ReactiVial. The mixture was reacted in an incubator for 3 days at 70° C. Then 0.2 ml glacial acetic acid, 2 ml chloroform, and 5 ml water were added. The mixture was vortexed to extract and centrifuged. The organic phase was washed with 5 ml water and transferred to a 15-ml round bottom polypropylene centrifuge tube. The crude product was evaporated to dryness. The product was isolated by silica gel chromatography. A 15 mm×12 mm i.d. glass column of silica gel was equilibrated with hexane. The crude product was dissolved in hexane and applied to the column, which was washed with 30 ml hexane. The product was eluted by adding 30 ml of 10% ethyl acetate in hexane. The product (14.95 mg) was evaporated to dryness.

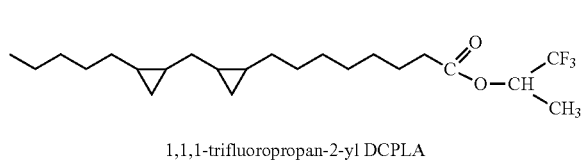 [SMILES: CCCCCC1CC1CC1CC1CCCCCCCC(=O)OC(C)C(F)(F)F]

1,1,1-trifluoropropan-2-yl DCPLA

Example 4: PKC-ε Activation by DCPLA-EtF3 Versus DCPLA Methyl Ester

Earlier research showed that DCPLA methyl ester is approximately 100 times more potent of a PKC-ε activator than unesterified DCPLA, with a maximum activation at 0.1 μM. Sen A, Alkon D L, Nelson T J, J. Biol. Chem. 287(19): 15947-58 (2012). PKC-ε activation by DCPLA-EtF3 was measured by measuring the incorporation of 32P-inorganic phosphate from gamma-32P-ATP by recombinant human PKC-ε. The results were compared to PKC-ε activation by DCPLA methyl ester and are shown in FIG. 1. As shown in FIG. 1, DCPLA-EtF3 had a peak PKC-ε activation at 0.1-1 nM, approximately 1000 times more potent than DCPLA methyl ester. This is potency approximately equal to that of bryostatin-1, which is one of the most potent PKC activators previously known. In addition, DCPLA-EtF3 produced approximately the same extent of activation as DCPLA methyl ester, while exhibiting this higher potency.

Example 5: PKC-ε Activation by 1,1,1-trifluoropropan-2-yl DCPLA

Figure 2:
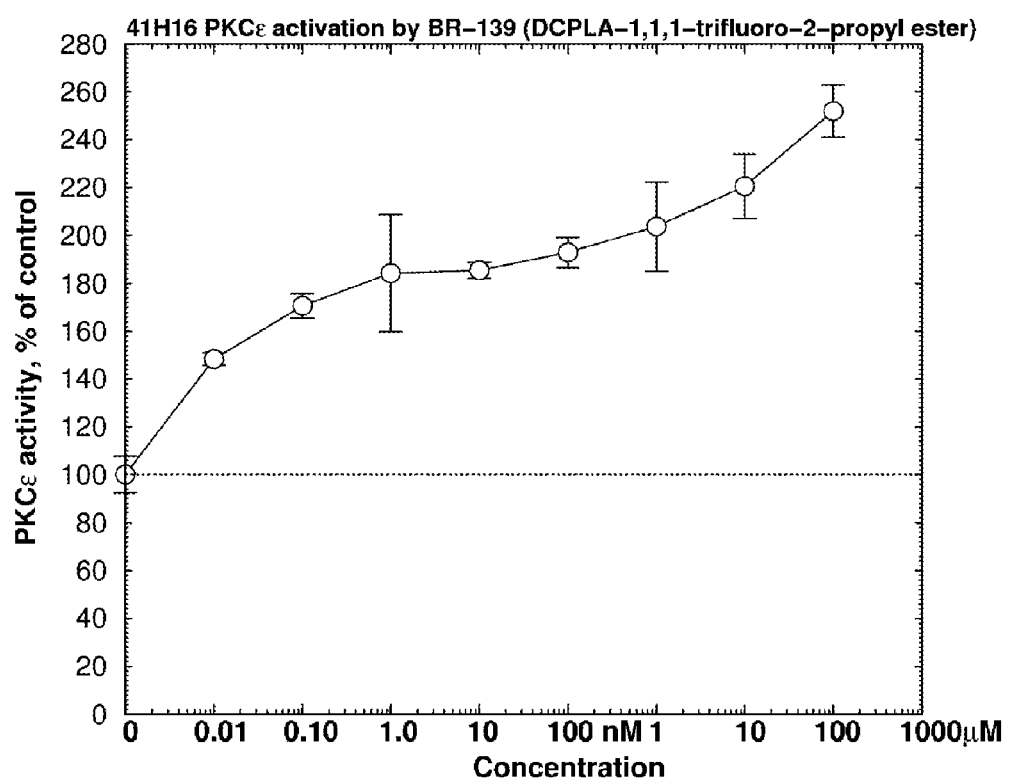
FIG. 2 shows PKC-ε activation by DCPLA-1,1,1-trifluoropropan-2-yl ester.

PKC-ε activation by 1,1,1-trifluoropropan-2-yl DCPLA was measured by measuring the incorporation of 32P-inorganic phosphate from gamma-32P-ATP by recombinant human PKC-ε. The results, shown in FIG. 2, show superior potency when compared to unmodified DCPLA. Activation started at 0.01 nM and was biphasic, consistent with a low and a high affinity binding site for DCPLA.

What is claimed is:

1. A compound chosen from a halogenated alkyl or aryl ester of an unsaturated fatty acid, wherein the unsaturated fatty acid is cyclopropanated, and wherein the alkoxy or aryloxy group of the ester comprises a —$CF_3$ group.

2. The compound of claim 1, wherein the unsaturated fatty acid is a polyunsaturated fatty acid chosen from linoleic acid, arachidonic acid, eicosadienoic acid, dihomo-gamma-linolenic acid, docosadienoic acid, adrenic acid, calendic acid, docosapentaenoic acid, jacaric acid, pinolenic acid, podocarpic acid, tetracosatetraenoic acid, tetracosapentaenoic acid, vernolic acid, docosahexaenoic acid, eicosapentaenoic acid, rumelenic acid, parinaric acid, linolenic acid, eicosenoic acid, mead acid, erucic acid, nervonic acid, rumenic acid, alpha-elostearic acid, catalpic acid, and punicic acid.

3. The compound of claim 1, wherein the unsaturated fatty acid is a monounsaturated fatty acid chosen from oleic acid and elaidic acid.

4. The compound of claim 1, wherein the halogenated ester is a halogenated alkyl ester.

5. The compound of claim 1, wherein the halogenated ester is a halogenated aryl ester.

6. The compound of claim 4, wherein the halogenated alkyl ester is chosen from halogenated methyl ester, ethyl ester, isopropyl ester, tert-butyl ester, and benzyl ester.

7. A halogenated alkyl or aryl ester of 8-[2-(2-pentylcyclopropylmethyl)-cyclopropyl]-octanoic acid (DCPLA), wherein the alkoxy or aryloxy group of the ester comprises a —$CF_3$ group.

8. The halogenated ester of claim 7, wherein the halogenated ester is a halogenated alkyl ester.

9. The halogenated ester of claim 7, wherein the halogenated ester is a halogenated aryl ester.

10. The halogenated ester of claim 8, wherein the halogenated alkyl ester is chosen from methyl ester, ethyl ester, isopropyl ester, tert-butyl ester, and benzyl ester.

11. The halogenated ester of claim 7, wherein the halogenated ester is a trifluoro alkyl ester.

12. The halogenated ester of claim 11, wherein the halogenated ester of DCPLA is chosen from 13. A composition comprising at least one halogenated alkyl or aryl ester of an unsaturated fatty acid and a pharmaceutically acceptable carrier, wherein the unsaturated fatty acid is cyclopropanated, and wherein the alkoxy or aryloxy group of the ester comprises a —CF group.

14. The composition of claim 13, wherein the unsaturated fatty acid is a polyunsaturated fatty acid chosen from linoleic acid, arachidonic acid, eicosadienoic acid, dihomo-gamma-linolenic acid, docosadienoic acid, adrenic acid, calendic acid, docosapentaenoic acid, jacaric acid, pinolenic acid, podocarpic acid, tetracosatetraenoic acid, tetracosapentaenoic acid, vernolic acid, docosahexaenoic acid, eicosapentaenoic acid, rumelenic acid, parinaric acid, linolenic acid, eicosenoic acid, mead acid, erucic acid, nervonic acid, rumenic acid, alpha-elostearic acid, catalpic acid, and punicic acid.

15. The composition of claim 13, wherein the unsaturated fatty acid is a monounsaturated fatty acid chosen from oleic acid and elaidic acid.

16. The composition of claim 13, wherein the at least one halogenated ester is a halogenated alkyl ester.

17. The composition of claim 13, wherein the at least one halogenated ester is a halogenated aryl ester.

18. The composition of claim 16, wherein the halogenated alkyl ester is chosen from methyl ester, ethyl ester, isopropyl ester, tert-butyl ester, and benzyl ester.

19. A composition comprising a halogenated alkyl or aryl ester of 8-[2-(2-pentylcyclopropylmethyl)-cyclopropyl]-octanoic acid (DCPLA) and a pharmaceutically acceptable carrier, wherein the alkoxy or aryloxy group of the ester comprises a —$CF_3$ group.

20. The composition of claim 19, wherein the halogenated ester is a halogenated alkyl ester.

21. The composition of claim 19, wherein the halogenated ester is a halogenated aryl ester.

22. The composition of claim 19, wherein the halogenated ester is a trifluoro alkyl ester.

23. The composition of claim 22, wherein the halogenated ester of DCPLA is chosen from

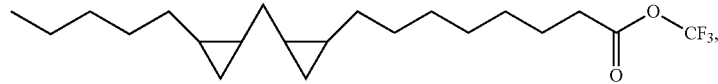

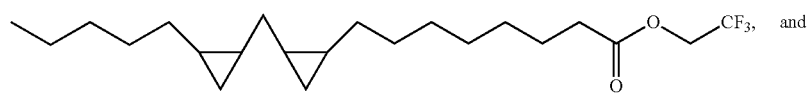

and

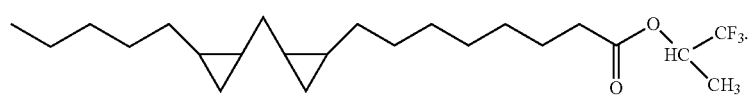

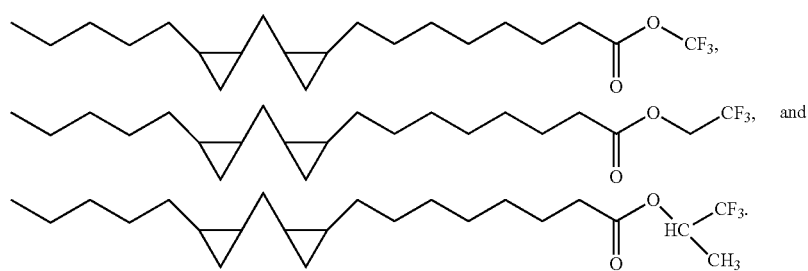
24. The compound of claim 1, wherein the ester is a trifluoro alkyl ester.
25. The composition of claim 13, wherein the ester is a trifluoro alkyl ester.
26. The composition of claim 20, wherein the halogenated alkyl ester is chosen from methyl ester, ethyl ester, isopropyl ester, tert-butyl ester, and benzyl ester.
* * * * *